United States Patent
Kearney et al.

(10) Patent No.: US 7,762,718 B2
(45) Date of Patent: Jul. 27, 2010

(54) CONDENSATION DETECTOR UTILIZING A WET BULB AND DRY BULB TEMPERATURE DIFFERENTIAL

(75) Inventors: Daniel J. Kearney, Ulster Park, NY (US); Mark A. Marnell, Kingston, NY (US); Kenneth A. Shadoff, Suwanee, GA (US); Randy J. Zoodsma, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 111 days.

(21) Appl. No.: 11/863,457

(22) Filed: Sep. 28, 2007

(65) Prior Publication Data

US 2009/0086789 A1   Apr. 2, 2009

(51) Int. Cl.
*G01N 25/62* (2006.01)
*G01K 7/00* (2006.01)
*G01K 3/00* (2006.01)

(52) U.S. Cl. .................. 374/27; 374/110; 374/163; 374/147; 374/166; 73/335.06

(58) Field of Classification Search ............. 374/28, 374/27, 16, 110, 166, 147, 141; 73/335.06
See application file for complete search history.

(56) References Cited

U.S. PATENT DOCUMENTS

| | | | |
|---|---|---|---|
| 2,845,790 A * | 8/1958 | Eddy | 73/25.05 |
| 4,129,250 A | 12/1978 | Chaikin et al. | |
| 4,279,150 A | 7/1981 | Land | |
| 4,523,860 A * | 6/1985 | Chin et al. | 374/27 |
| 4,981,369 A * | 1/1991 | Kumada et al. | 374/28 |
| 4,996,993 A | 3/1991 | York | |
| 5,123,478 A * | 6/1992 | Hosaka | 165/292 |
| 5,520,048 A | 5/1996 | Traina et al. | |
| 5,934,368 A * | 8/1999 | Tanaka et al. | 165/233 |
| 6,014,890 A | 1/2000 | Breen | |
| 7,174,738 B2 * | 2/2007 | Scott | 62/259.2 |
| 2008/0083526 A1* | 4/2008 | Young et al. | 165/11.1 |

\* cited by examiner

*Primary Examiner*—Gail Verbitsky
*Assistant Examiner*—Mirellys Jagan
(74) *Attorney, Agent, or Firm*—Cantor Colburn LLP; Geraldine Monteleone

(57) ABSTRACT

Apparatus, systems and methods for coordinated detecting condensation utilizing a wet bulb and dry bulb temperature differential are disclosed. According to exemplary embodiments, a condensation detector may include; a first temperature sensor which generates a first temperature signal corresponding to a temperature measured at the first temperature sensor, a second temperature sensor which generates a second temperature signal corresponding to a temperature measured at the second temperature sensor, a connector having a first end connected to the first temperature sensor, and a detector which receives the first and the second temperature signals and determines the presence of condensation at a second end of the connector based on differences between the first and second temperature signals.

19 Claims, 2 Drawing Sheets

CONDENSATION DETECTOR UTILIZING A WET BULB AND DRY BULB TEMPERATURE DIFFERENTIAL

BACKGROUND OF THE INVENTION

1. Field of the Invention

This invention relates to a device and method for detecting the presence of condensation on cooling apparatus. Particularly, the invention relates to a device and method for detecting the presence of the condensation using measurements from a wet bulb and a dry bulb and determining a temperature differential.

2. Description of the Related Art

The current state of high power density computing has reached a stage where forced air is no longer feasible or practical for computer cooling needs. Forced air cooling does not provide a sufficient thermal capacity to adequately cool the various heat-producing components of today's high power density computers.

In order to provide a greater cooling capacity the use of a relatively low temperature cooling liquid, usually water, has been introduced. The low temperature cooling liquid is pumped through piping which runs throughout the high temperature regions of the computer. The cooling liquid has a greater thermal capacity than air and therefore can adequately absorb and remove thermal energy from the various heat-producing components of the computer. The cooling liquid is then transported to a lower temperature environment, e.g., a heat exchanger, where it radiates the absorbed thermal energy before it is returned to the heat producing components of the computer.

Unfortunately, the use of relatively low temperature cooling liquid gives rise to the potential for condensation to occur. When a data center environment's effective dew point temperature is at or below the cooling liquid temperature, condensation of water from the air in the data center environment will form on the cooling liquid piping. The accumulation of water from condensation in a high power density computer is not desirable as it could cause equipment failures, or, in an extreme situation, even cause a potential safety concern.

One method of preventing condensation is to place insulation around the cooling liquid piping. While the insulation can help to minimize condensation, it is bulky and requires space that is generally not available in a high power density computer. Insulation may also be relatively expensive and difficult to apply. Furthermore, use of insulation generally eliminates any radiative cooling through use of ambient air.

Therefore, what are needed are apparatus and methods for operating a cooling liquid system in a data center that alerts a user to the presence of condensation, and/or reactively eliminates such condensation, such as those disclosed therein.

SUMMARY OF THE INVENTION

The shortcomings of the prior art may be overcome and additional advantages may be provided through the provision of a condensation detector utilizing a wet bulb and dry bulb temperature differential.

According to exemplary embodiments, a condensation detector includes; a first temperature sensor which provides a first temperature signal corresponding to one of a dry bulb temperature and a wet bulb temperature measured at the first temperature sensor, a second temperature sensor which provides a second temperature signal corresponding to a dry bulb temperature measured at the second temperature sensor, and a detector which receives the first and the second temperature signals, compares the first and second temperature signals and determines the presence of condensation based on the comparison of the first and second temperature signals.

According to exemplary embodiments, a cooling liquid system includes; cooling liquid piping, a first temperature sensor which generates a first temperature signal corresponding to a temperature measured at the first temperature sensor, wherein the first temperature sensor is connected to the cooling liquid piping, a second temperature sensor which generates a second temperature signal corresponding to a temperature measured at the first temperature sensor disposed substantially adjacent to the first temperature sensor, and a detector which receives the first and the second temperature signals and determines the presence of condensation on the cooling liquid piping based on differences between the first and second temperature signals.

According to exemplary embodiments, a method of detecting condensation on a surface includes; generating a first temperature signal from a first temperature sensor corresponding to a temperature measured at the first temperature sensor, generating a second temperature signal from a second temperature sensor corresponding to a temperature measured at the second temperature sensor, and determining the presence of condensation on the surface based on differences between the first and second temperature signals.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

The detailed description explains the exemplary embodiments of the invention, together with advantages and features, by way of example with reference to the drawings.

DETAILED DESCRIPTION OF THE INVENTION

Hereinafter, exemplary embodiments will be described in more detail with reference to the attached drawings.

Figure 1:
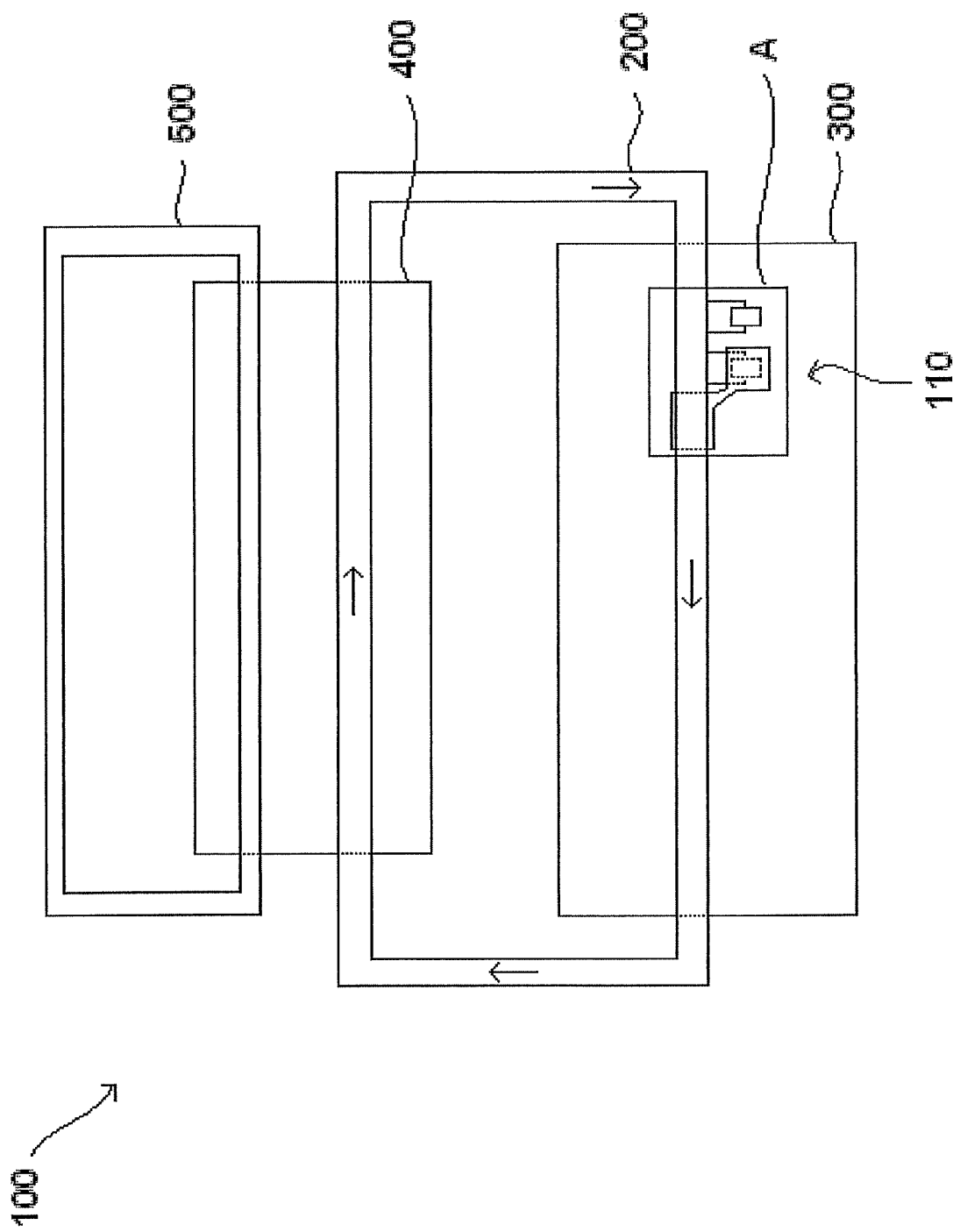
FIG. 1 is a diagram illustrating one example of a cooling liquid system including a condensation detector that can be implemented within embodiments of the present invention.

Turning now to the drawings in greater detail, it will be seen that in FIG. 1 there is a diagram illustrating one example of a cooling liquid system 100 including a condensation detector 110 that can be implemented within the embodiments of the present invention.

The cooling liquid system 100 includes cooling liquid piping 200 which transports a cooling liquid (not shown) to a high temperature region of a computer 300. The cooling liquid piping 200 may be any pathway for transporting the cooling liquid. Exemplary embodiments of the cooling liquid include water, ammonia, carbinol, acetone, heptane or any combination thereof. In addition, exemplary embodiments of the cooling liquid may include thermally conductive particles disposed in suspension therein. Other cooling liquids, such as other commercially available refrigerants, may be used.

The cooling liquid of the cooling liquid system 100 absorbs heat from the high temperature region of the high-density computer 300 (which may be, for example, a high power density computer) thereby cooling the high temperature region. Subsequently, the heated cooling liquid is transported away from the high temperature region and towards a heat exchanger 400 along the direction of the arrows as shown in FIG. 1. The heated cooling liquid is cooled in the heat exchanger 400 before again being transported to the high temperature region of the computer 300. This configuration allows for the same cooling liquid to be used repeatedly to cool the high temperature region of the high-density computer 300.

In the exemplary embodiment shown in FIG. 1 the heat exchanger 400 allows for the exchange of heat from the heated cooling liquid to a secondary cooling liquid (not shown) transported by a secondary loop of cooling liquid piping 500. The heat exchanger 400 and the secondary loop of cooling liquid piping 500 may be used to regulate the temperature of the cooling liquid input to the computer 300. However, alternative exemplary embodiments include configurations wherein the heat exchanger 400 and/or the secondary loop of cooling liquid piping 500 are omitted. In such an alternative exemplary embodiment, the cooling liquid in the cooling liquid piping 200 may be cooled simply by transporting the cooling liquid to a lower temperature region of the computer 300 before again being transported to the high temperature region. In another alternative exemplary embodiment cooling liquid may be passed through the high temperature region in an open loop wherein little or none of the cooling liquid is recycled.

Figure 2:
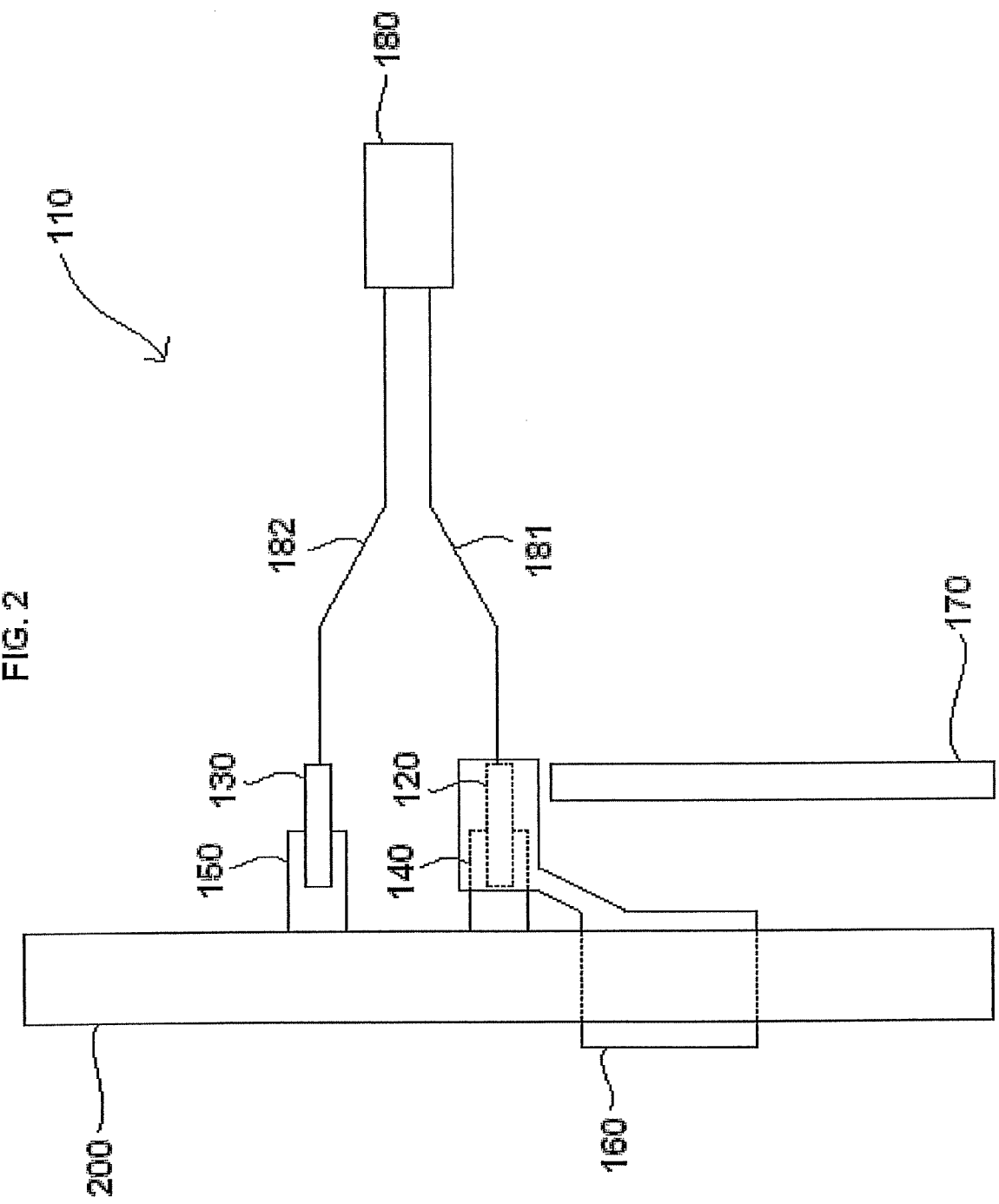
FIG. 2 is a magnified view of the region "A" shown in FIG. 1.

Referring now to FIGS. 1 and 2, the cooling liquid system 100 includes a condensation detector 110. The condensation detector 110 includes a first temperature sensor 120 and a second temperature sensor 130. In the current exemplary embodiment the first and second temperature sensors are thermistors which have a resistance which varies with temperature. Alternative exemplary embodiments include configurations wherein the temperature sensors 120 and 130 are other temperature measuring devices such as thermocouples. Other temperature sensors are known in the art and may be used as appropriate.

In the present exemplary embodiment the first and second temperature sensors 120 and 130 are disposed on first and second mounting brackets 140 and 150, respectively, which are in turn mounted on the cooling liquid piping 200. The mounting brackets 140 and 150 insulate the first and second temperature sensors 120 and 130 from the cooling liquid piping 200. In one exemplary embodiment, the first and second mounting brackets 140 and 150 are made from an insulating material, exemplary embodiments of which include plastic. In another exemplary embodiment the first and second mounting brackets 140 and 150 may be formed together in a single unit.

The first and second temperature sensors 120 and 130, and their corresponding mounting brackets 140 and 150, may be disposed within a temperature zone wherein the temperature exhibits substantial uniformity.

A connector 160 is formed between the first temperature sensor 120 and the cooling liquid piping 200. This connector 160 allows condensation, if present, to flow from the cooling liquid piping 200 to the first temperature sensor 120. In one exemplary embodiment, the connector 160 is a wick formed from a wicking material; in such an embodiment capillary action of the wick draws any condensation which may be present to the first temperature sensor 120, thereby creating a wet bulb temperature sensor. In such an exemplary embodiment, the wick may be wrapped substantially around the cooling liquid piping 200 and the first temperature sensor 120. In another exemplary embodiment the first temperature sensor 120 may be disposed below the cooling liquid piping 200 and wicking action of the wick may be assisted by gravity, e.g., the first temperature sensor 120 may be formed at a lesser gravitational potential than the cooling liquid piping 200 and the wick.

In one exemplary embodiment the wick material can be mounted and kept in contact with the cooling liquid piping 200 via a mounting structure (not shown) which can snap around the cooling liquid piping 200, thereby pinching the wicking material between the plastic structure and the cooling liquid piping 200 with adequate space to allow wicking. In one exemplary embodiment the mounting structure may be formed of plastic. In one exemplary embodiment the mounting structure may be formed unitarily with either or both of the mounting brackets 140 and 150, thereby forming a structure capable of mounting the wick and the temperature sensors 120 and 130 all in one structure. In one exemplary embodiment the wick material may be a high absorbency hydroentangled non-woven cellulose/polymer material. In another exemplary embodiment the wick material may be any suitable material as known in the art.

The wick material at the surface of the cooling liquid piping 200 collects any condensation from the cooling liquid piping 200 and by capillary action moves that condensation through the wicking material to the first temperature sensor 120. The wick material and its structure therefore bridges from the surface of the cooling liquid piping 200 to the surface of the first temperature sensor 120. Therefore, any potential condensation present on the local cooling liquid piping 200 may become a source of water to create a wet bulb temperature sensor as described in more detail below.

In the exemplary embodiment wherein the connector 160 is a wick, the condensation detector 110 may further include an air baffle 170 disposed between the wick and an airflow path within the condensation detector 110. The air baffle 170 minimizes contamination of the wick material from the environment surrounding the condensation detector 110. The air baffle 170 basically prevents the surrounding air from prematurely drying the wick through evaporation and prevents contaminants from attaching to the wick material. In one exemplary embodiment, the air baffle 170 may be disposed on the cooling liquid piping 200. Alternative exemplary embodiments include configurations wherein the air baffle 170 is disposed in connection with one of the mounting brackets 140 or 150. In another exemplary embodiment the air baffle 170 may be formed as part of the unitary plastic structure described above. Alternative exemplary embodiments include configurations wherein the air baffle 170 is omitted.

The first and second temperature sensors 120 and 130 are electrically connected to a detector 180 via first and second wiring 181 and 182, respectively. The detector 180 receives a first temperature signal corresponding to a temperature measured at the first temperature sensor 120 via the first wiring 181 and receives a second temperature signal corresponding to a temperature measured at the second temperature sensor 130 via the second wiring 182. After receiving the first and second temperature signals, the detector then compares the first and second temperature signals and determines the presence of condensation as will be described in more detail below. Exemplary embodiments of the detector 180 may be digital or analog.

Referring now to FIGS. 1 and 2 and tables 1-3, an exemplary method of detecting condensation on a surface of the cooling liquid piping 200 will be described in more detail.

Data center environments in which computers operate may exhibit a range of ambient temperatures and ambient relative humidities as shown in Table 1.

TABLE 1

| DEWPOINT TEMPERATURE (C.) | | | | | | | | | | |
|---|---|---|---|---|---|---|---|---|---|---|
| AMBIENT | 50 | 10.08 | 20.88 | 27.65 | 32.66 | 36.69 | 40.07 | 42.99 | 45.57 | 47.89 | 50.00 |
| TEMP. | 45 | 6.37 | 16.84 | 23.29 | 28.25 | 32.14 | 35.41 | 38.23 | 40.73 | 42.97 | 45.00 |
| (C.) | 40 | 2.63 | 12.78 | 19.12 | 23.82 | 27.58 | 30.74 | 33.47 | 35.88 | 38.04 | 40.00 |
| | 35 | −1.00 | 8.71 | 14.84 | 19.38 | 23.02 | 26.07 | 28.70 | 31.02 | 33.11 | 35.00 |
| | 32 | −3.00 | 6.25 | 12.27 | 16.72 | 20.28 | 23.26 | 25.84 | 28.11 | 30.15 | 32.00 |
| | 30 | −4.35 | 4.61 | 10.55 | 14.94 | 18.45 | 21.39 | 23.93 | 26.17 | 28.18 | 30.00 |
| | 25 | −7.74 | 0.50 | 6.24 | 10.48 | 13.86 | 16.70 | 19.15 | 21.31 | 23.24 | 25.00 |
| | 20 | −11.18 | −3.21 | 1.92 | 6.01 | 9.27 | 12.01 | 14.37 | 16.45 | 18.31 | 20.00 |
| | 15 | −14.66 | −6.90 | −2.14 | 1.52 | 4.67 | 7.31 | 9.58 | 11.58 | 13.37 | 15.00 |
| | 10 | −18.18 | −10.63 | −6.01 | −2.63 | 0.06 | 2.60 | 4.79 | 6.71 | 8.44 | 10.00 |
| | 5 | −21.74 | −14.43 | −9.92 | −6.64 | −4.03 | −1.87 | −0.01 | 1.84 | 3.50 | 5.00 |
| | 0 | −25.34 | −18.23 | −13.87 | −10.69 | −8.16 | −6.06 | −4.26 | −2.68 | −1.27 | 0.00 |
| | | 10 | 20 | 30 | 40 | 50 | 60 | 70 | 80 | 90 | 100 |
| | | | | | AMBIENT RELATIVE HUMIDITY % | | | | | | |

Optimal data center environmental conditions range from about 20° C. to about 25° C. and from about 40% relative humidity to about 60% relative humidity, however a typical data center environment may range beyond these optimal conditions to anywhere from about 10° C. to about 32° C. and from about 20% relative humidity to about 80% relative humidity. As shown in Table 1, condensation may form on any surface which is at or below the dew point temperature for a given ambient temperature and relative humidity, e.g., if the ambient temperature and the ambient relative humidity in the data center environment are 25° C. and 40%, respectively, any surface with a temperature below 10.48° C. will tend to form condensation thereon.

However, when condensation is present on the cooling liquid piping 200 the moisture from the condensation is transported via the connector 160 to the first temperature sensor 120. The moisture from the condensation transforms the first temperature sensor 120 into a wet bulb thermometer. As shown in Table 2, at any relative humidity less than 100% a wet bulb temperature measured by a wet bulb thermometer is significantly less than the ambient temperature due to evaporation of the moisture from around the wet bulb thermometer, e.g., if the ambient temperature and the ambient relative humidity in the data center environment are 25° C. and 40%, respectively, the wet bulb thermometer will measure a temperature of 16.33° C.

TABLE 2

| WET BULB (C.) | | | | | | | | | | |
|---|---|---|---|---|---|---|---|---|---|---|
| AMBIENT | 50 | 24.15 | 28.72 | 32.58 | 35.93 | 38.87 | 41.52 | 43.92 | 46.10 | 48.12 | 50.00 |
| TEMP. | 45 | 21.50 | 25.50 | 28.90 | 31.95 | 34.65 | 37.09 | 39.30 | 41.35 | 43.23 | 45.00 |
| (C.) | 40 | 18.87 | 22.30 | 25.30 | 28.00 | 30.43 | 32.65 | 34.70 | 36.60 | 38.35 | 40.00 |
| | 35 | 16.21 | 19.10 | 21.71 | 24.08 | 26.26 | 28.26 | 30.12 | 31.85 | 33.47 | 35.00 |
| | 32 | 14.58 | 17.19 | 19.58 | 21.75 | 23.77 | 25.64 | 27.39 | 29.02 | 30.56 | 32.00 |
| | 30 | 13.48 | 15.91 | 18.15 | 20.20 | 22.11 | 23.90 | 25.57 | 27.13 | 28.61 | 30.00 |
| | 25 | 10.68 | 12.69 | 14.58 | 16.33 | 17.99 | 19.54 | 21.02 | 22.41 | 23.74 | 25.00 |
| | 20 | 7.79 | 9.44 | 10.99 | 12.47 | 13.87 | 15.21 | 16.49 | 17.71 | 18.88 | 20.00 |
| | 15 | 4.77 | 6.09 | 7.36 | 8.58 | 9.75 | 10.88 | 11.97 | 13.01 | 14.02 | 15.00 |
| | 10 | 1.60 | 2.65 | 3.66 | 4.65 | 5.61 | 6.53 | 7.44 | 8.32 | 9.17 | 10.00 |
| | 5 | N/A | N/A | N/A | N/A | N/A | N/A | N/A | N/A | N/A | 5.00 |
| | 0 | N/A | N/A | N/A | N/A | N/A | N/A | N/A | N/A | N/A | 0.00 |
| | | 10 | 20 | 30 | 40 | 50 | 60 | 70 | 80 | 90 | 100 |
| | | | | | AMBIENT RELATIVE HUMIDITY % | | | | | | |

In order to detect such condensation, the first temperature sensor 120 and the second temperature sensor 130 send the first and second temperature signals to the detector 180. When there is substantially no detectable condensation on the cooling liquid piping 200, the first and the second temperature sensors both act as dry bulb thermometers measuring dry bulb temperatures substantially equal to the ambient temperature, and therefore because the first and second temperature sensors 120 and 130 are disposed within a substantially uniform temperature zone, the first and second temperature signals sent by the first and second temperature sensors 120 and 130 are substantially equal. In such a situation, the detector 180 interprets the lack of a sufficient temperature differentiation between the first and second temperature signals as an absence of condensation.

Therefore, the first temperature sensor, which in the presence of condensation acts like a wet bulb thermometer, will measure a temperature significantly less than the temperature measured by the second temperature sensor which continues to act as a dry bulb thermometer. The temperature differential between a dry bulb thermometer and a wet bulb thermometer is shown in Table 3 for a variety of data center environmental conditions. As can be seen in Table 3, the difference between a dry bulb temperature measurement and a wet bulb temperature measurement in typical data center environmental conditions ranges from about 1.7° C. to about 14.81° C. and in optimal data center environmental conditions the difference ranges from about 4.8° C. to about 8.7° C.

TABLE 3

| | | \multicolumn{10}{c}{DIFFERENCE BETWEEN WET BULB AND DRY BULB (C.)} |
|---|---|---|---|---|---|---|---|---|---|---|
| AMBIENT TEMP. (C.) | 50 | 25.85 | 21.28 | 17.42 | 14.07 | 11.13 | 8.48 | 6.08 | 3.90 | 1.88 | 0.00 |
| | 45 | 23.50 | 19.50 | 16.10 | 13.05 | 10.35 | 7.91 | 5.70 | 3.65 | 1.77 | 0.00 |
| | 40 | 21.13 | 17.70 | 14.70 | 12.00 | 9.57 | 7.35 | 5.30 | 3.40 | 1.65 | 0.00 |
| | 35 | 18.79 | 15.90 | 13.29 | 10.92 | 8.74 | 6.74 | 4.88 | 3.15 | 1.53 | 0.00 |
| | 32 | 17.42 | 14.81 | 12.42 | 10.25 | 8.23 | 6.36 | 4.61 | 2.98 | 1.44 | 0.00 |
| | 30 | 16.52 | 14.09 | 11.85 | 9.80 | 7.89 | 6.10 | 4.43 | 2.87 | 1.39 | 0.00 |
| | 25 | 14.32 | 12.31 | 10.42 | 8.67 | 7.01 | 5.46 | 3.98 | 2.59 | 1.26 | 0.00 |
| | 20 | 12.21 | 10.56 | 9.01 | 7.53 | 6.13 | 4.79 | 3.51 | 2.29 | 1.12 | 0.00 |
| | 15 | 10.23 | 8.91 | 7.64 | 6.42 | 5.25 | 4.12 | 3.03 | 1.99 | 0.98 | 0.00 |
| | 10 | 8.40 | 7.35 | 6.34 | 5.35 | 4.39 | 3.47 | 2.56 | 1.68 | 0.83 | 0.00 |
| | 5 | N/A | N/A | N/A | N/A | N/A | N/A | N/A | N/A | N/A | N/A |
| | 0 | N/A | N/A | N/A | N/A | N/A | N/A | N/A | N/A | N/A | N/A |
| | | 10 | 20 | 30 | 40 | 50 | 60 | 70 | 80 | 90 | 100 |
| | | \multicolumn{10}{c}{AMBIENT RELATIVE HUMIDITY %} |

Similar to when there is substantially no condensation present, the first temperature sensor 120 transmits the first temperature signal corresponding to the temperature measured at the first temperature sensor 120 to the detector 180 and the second temperature sensor 130 transmits the second temperature signal corresponding to the temperature measured at the second temperature sensor 130. However, when condensation is present, the first temperature signal may be significantly different from the second temperature signal due to the first temperature sensor 120 acting as a wet bulb thermometer and the second temperature sensor 130 acting as a dry bulb thermometer.

The detector 180 then receives the first and second temperature signals, compares them and determines whether condensation is present based on the difference between the first and second temperature signals. The detector 180 may be calibrated to determine that condensation is present whenever the difference between the first and second temperature signals is equal to or greater than a predetermined threshold. In one exemplary embodiment, the threshold corresponds to a temperature difference of about 1.6° C. In another exemplary embodiment the threshold corresponds to a temperature difference of equal to or less than 0.75° C.

In one exemplary embodiment, the first and second temperature sensors 120 and 130 may be calibrated to adjust for small temperature variations due to the slightly different positioning of the first and second temperature sensors 120 and 130 within the condensation detector 110.

In one exemplary embodiment, when the detector 180 detects a temperature differential equal to or greater than the predetermined threshold and determines that condensation is present on the cooling liquid piping 200, the detector 180 may notify a user that condensation is present. The detector 180 may notify the user through various means well known in the art such as audio and/or visual signals or error codes delivered to the user through graphical interfaces.

In another exemplary embodiment, when the detector 180 detects a temperature differential equal to or greater than the predetermined threshold and determines that condensation is present on the cooling liquid piping 200, the detector 180 may adjust the temperature of the liquid flowing through the secondary cooling liquid piping 500 to increase the temperature of the liquid flowing through the cooling liquid piping 200. The temperature of the liquid in the secondary liquid piping 500 may be increased to the point where the temperature of the cooling liquid piping 200 is above the dew point within the data center environment, thus preventing the formation of additional condensation and eliminating the condensation which is already present. Similarly, the condensation detector 110 would detect situations wherein the temperature in the secondary liquid piping 500 is too low.

In another exemplary embodiment, when the detector 180 detects a temperature differential equal to or greater than the predetermined threshold and determines that condensation is present on the cooling liquid piping 200, the detector 180 may activate a fan (not shown) or may turn off the computer 300. Alternative exemplary embodiments include configurations wherein the detector 180 initiates a procedure wherein the condensation is eliminated or wherein the danger to the computer 300 is otherwise eliminated, e.g., by turning off the sections of the computer 300 wherein the condensation is detected.

Although the previous description has related to a cooling liquid system 100 including a single condensation detector 110, alternative exemplary embodiments include configurations wherein the cooling liquid system 100 includes a plurality of condensation detectors 110. In such alternative exemplary embodiments the plurality of condensation detectors 110 may be disposed throughout the cooling liquid piping 200 and also may be disposed on the secondary cooling liquid piping 500.

Although the condensation detector 110 has been described with reference to the cooling liquid system 100 including a computer 300, it would be apparent to one of ordinary skill in the art that the condensation detector 110 may be applied to any situation wherein the detection of condensation on a surface is desirable.

While the preferred embodiments to the invention have been described, it will be understood that those skilled in the art, both now and in the future, may make various improvements and enhancements which fall within the scope of the claims which follow. These claims should be construed to maintain the proper protection for the invention first described.

What is claimed is:

1. A condensation detector comprising:
   a first temperature sensor which provides a first temperature signal corresponding to one of a dry bulb temperature and a wet bulb temperature measured at an external surface of a pipe;
   a second temperature sensor which provides a second temperature signal corresponding to a dry bulb temperature measured at the external surface of the pipe; and
   a detector which receives the first and the second temperature signals, compares the first and second temperature signals and determines the presence of condensation on the external surface of the pipe based on the comparison of the first and second temperature signals.

2. The condensation detector of claim 1, wherein the first temperature sensor comprises a first thermistor and the second temperature sensor comprises a second thermistor.

3. The condensation detector of claim 1, further comprising a wick connected to the first temperature sensor.

4. The condensation detector of claim 3, further comprising a baffle disposed between the wick and an airflow path.

5. The condensation detector of claim 3, wherein the wick material is a high absorbency hydroentangled non-woven cellulose material.

6. A cooling liquid system comprising:
cooling liquid piping having an external surface;
a first temperature sensor which generates a first temperature signal corresponding to a temperature measured at the first temperature sensor, wherein the first temperature sensor is operatively connected to the external surface of the cooling liquid piping, the first temperature sensor not extending into the cooling liquid piping;
a second temperature sensor which generates a second temperature signal corresponding to a temperature measured at the first temperature sensor disposed substantially adjacent to the first temperature sensor on the external surface of the cooling liquid piping, the second temperature sensor not extending into the cooling liquid piping; and
a detector which receives the first and the second temperature signals and determines the presence of condensation on the external surface of the cooling liquid piping based on differences between the first and second temperature signals.

7. The cooling liquid system of claim 6, wherein the first temperature sensor is disposed on a first insulating mounting bracket, the first insulating bracket is disposed on the external surface of the cooling liquid piping, the second temperature sensor is disposed on a second insulating bracket and the second insulating bracket is disposed on the external surface of the cooling liquid piping.

8. The cooling liquid system of claim 6, wherein the first temperature sensor comprises a first thermistor and the second temperature sensor comprises a second thermistor.

9. The cooling liquid system of claim 6, further comprising:
a secondary cooling fluid loop radiatively coupled to the cooling liquid piping, wherein the secondary cooling fluid loop heats a fluid in the cooling liquid piping when the differences between the first and second temperature signals exceed a predetermined amount.

10. The cooling liquid system of claim 6, wherein the detector notifies a user when the differences between the first and second temperature signals exceed a predetermined amount.

11. The cooling liquid system of claim 6, wherein the detector turns off power to a computer when the differences between the first and second temperature signals exceed a predetermined amount.

12. The cooling liquid system of claim 6, wherein the first temperature sensor is connected to the external surface of the cooling liquid piping via a wick.

13. The cooling liquid system of claim 12, wherein the first temperature sensor is disposed at a lesser gravitational potential than the wick.

14. The cooling liquid system of claim 12, further comprising an air baffle disposed between the wick and an air flow path.

15. A method of detecting condensation on a surface, the method comprising:
fluidly connecting a first temperature sensor to an external surface;
generating a first temperature signal from the first temperature sensor corresponding to a temperature measured at the first temperature sensor;
fluidly connecting a second temperature sensor to the external surface;
generating a second temperature signal from the second temperature sensor corresponding to a temperature measured at the second temperature sensor; and
determining the presence of condensation on the external surface based on differences between the first and second temperature signals.

16. The method of detecting the presence of condensation of claim 15, wherein the fluidly connecting the first temperature sensor to the external surface comprises connecting a wick between the first temperature sensor and the external surface.

17. The method of detecting the presence of condensation of claim 15, further comprising: turning off power to a computer when the differences between the first and second temperature signals exceed a predetermined amount.

18. The method of detecting the presence of condensation of claim 15, wherein the wherein the fluidly connecting the first temperature sensor to the external surface comprises operatively connecting the first temperature sensor to the external surface of a cooling liquid pipe, and wherein the fluidly connecting the second temperature sensor to the external surface comprises operatively connecting the second temperature sensor to the external surface of a cooling liquid pipe.

19. The method of detecting the presence of condensation of claim 18, further comprising: heating fluid in the cooling liquid pipe with a secondary cooling fluid loop radiatively coupled to the cooling liquid pipe when the differences between the first and second temperature signals exceed a predetermined amount.

* * * * *